United States Patent
Wyatt et al.

(10) Patent No.: US 7,511,025 B2
(45) Date of Patent: Mar. 31, 2009

(54) COMPOSITIONS AND METHODS FOR INHIBITING THE SYNTHESIS OR EXPRESSION OF MMP-1

(75) Inventors: Colby Wyatt, West Lebanon, NH (US); Constance F. Brinckerhoff, New London, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/628,829

(22) PCT Filed: Jun. 10, 2005

(86) PCT No.: PCT/US2005/020470

§ 371 (c)(1),
(2), (4) Date: Feb. 23, 2007

(87) PCT Pub. No.: WO2006/088483

PCT Pub. Date: Aug. 24, 2006

(65) Prior Publication Data

US 2007/0237757 A1 Oct. 11, 2007

Related U.S. Application Data

(60) Provisional application No. 60/580,181, filed on Jun. 16, 2004, provisional application No. 60/645,206, filed on Jan. 20, 2005.

(51) Int. Cl.
*A61K 31/70* (2006.01)
*C07H 21/04* (2006.01)

(52) U.S. Cl. .................. 514/44; 536/23.1; 536/24.5

(58) Field of Classification Search .................. None
See application file for complete search history.

(56) References Cited

U.S. PATENT DOCUMENTS

2003/0105044 A1  6/2003  Baker et al.

FOREIGN PATENT DOCUMENTS

| WO | WO 0170950 | 9/2001 |
|---|---|---|
| WO | WO 0270950 | 9/2002 |
| WO | WO 2004061423 A2 * | 7/2004 |

OTHER PUBLICATIONS

Ambion Technical Bulletin #506, [online], [retrieved on May 29, 2008] Retrieved from the internet <URL: http://www.ambion.com/techlib/tb/tb_506.html>.*

Ambion siRNA target finder, [online], [retrieved on May 29, 2008] Retrieved from the internet <URL: http://www.ambion.com/techlib/misc/siRNA_finder.html>.* protocol-online.org RNAi design tools, [online], [retrieved on May 29, 2008] Retrieved from the internet <URL: http://www.protocol-online.org/prot/Molecular_Biology/RNA/RNA_Interference_RNAi_/siRNA_Design_Rules>.*

Ambion design tool for pSilencer vector, [online], [retrieved on May 29, 2008] Retrieved from the internet <URL: http://www.ambion.com/techlib/misc/psilencer_converter.html>.*

Durko et al., "Suppression of basement membrane type IV collagen degradation and cell invasion in human melanoma cells expressing an antisense RNA for MMP-1", Biochimica et Biophysica Acta 1356 1997 271-280.

Jiang et al., "Inhibition of MMP-1 expression by antisense RNA decreases invasiveness of human chondrosarcoma", Journal of Orthopaedic Research 21 2003 1063-1070.

Bertrand et al., "Comparison of antisense oligonucleotides and siRNAs in cell culture and in vivo", Biochemical and Biophysical Research Communications 296 2002 1000-1004.

* cited by examiner

*Primary Examiner*—Tracy Vivlemore
(74) *Attorney, Agent, or Firm*—Licata & Tyrrell P.C.

(57) ABSTRACT

The present invention relates to the specific inhibition of matrix metalloproteinase 1 (MMP-1) using agents which inhibit the synthesis or expression of MMP-1. Such agents are useful for suppressing invasion or metastasis of a tumor cell and in the treatment, prevention and management of cancer.

3 Claims, No Drawings

```
                        SEQUENCE LISTING

<160> NUMBER OF SEQ ID NOS: 20

<210> SEQ ID NO 1
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 1
gatccccacc agatgctgaa accctgttca agagacaggg tttcagcatc tggtttttg      60 gaaa                                                                  64

<210> SEQ ID NO 2
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 2
agcttttcca aaaaccaga tgctgaaacc ctgtctcttg aacagggttt cagcatctgg      60
tggg                                                                  64

<210> SEQ ID NO 3
<211> LENGTH: 1973
<212> TYPE: DNA
<213> ORGANISM: Homo sapiens

<400> SEQUENCE: 3
```

```
gggatattgg agtagcaaga ggctgggaag ccatcactta ccttgcactg agaaagaaga      60
caaaggccag tatgcacagc tttcctccac tgctgctgct gctgttctgg ggtgtggtgt     120
ctcacagctt cccagcgact ctagaaacac aagagcaaga tgtggactta gtccagaaat     180
acctggaaaa atactacaac ctgaagaatg atgggaggca agttgaaaag cggagaaata     240
gtggcccagt ggttgaaaaa ttgaagcaaa tgcaggaatt ctttgggctg aaagtgactg     300
ggaaaccaga tgctgaaacc ctgaaggtga tgaagcagcc cagatgtgga gtgcctgatg     360
tggctcagtt tgtcctcact gaggggaacc ctcgctggga gcaaacacat ctgacctaca     420
ggattgaaaa ttacacgcca gatttgccaa gagcagatgt ggaccatgcc attgagaaag     480
ccttccaact ctggagtaat gtcacacctc tgacattcac caaggtctct gagggtcaag     540
cagacatcat gatatctttt gtcaggggag atcatcggga caactctcct tttgatggac     600
ctggaggaaa tcttgctcat gcttttcaac aggcccagga tattggaggg gatgctcatt     660
ttgatgaaga tgaaaggtgg accaacaatt cagagagta caacttacat cgtgttgcgg     720
ctcatgaact cggccattct cttggactct cccattctac tgatatcggg gctttgatgt     780
accctagcta caccttcagt ggtgatgttc agctagctca ggatgacatt gatggcatcc     840
aagccatata tggacgttcc caaaatcctg tccagcccat cggcccacaa accccaaaag     900
cgtgtgacag taagctaacc tttgatgcta taactacgat tcggggagaa gtgatgttct     960
ttaaagacag attctacatg cgcacaaatc ccttctaccc ggaagttgag ctcaatttca    1020
tttctgtttt ctggccacaa ctgccaaatg ggcttgaagc tgcttacgaa tttgccgaca    1080
gagatgaagt ccggttttc aaagggaata agtactgggc tgttcaggga cagaatgtgc    1140
tacacggata ccccaaggac atctacagct cctttggctt ccctagaact gtgaagcata    1200
tcgatgctgc tctttctgag gaaaacactg gaaaaaccta cttctttgtt gctaacaaat    1260
actggaggta tgatgaatat aaacgatcta tggatccagg ttatcccaaa atgatagcac    1320
atgactttcc tggaattggc cacaaagttg atgcagtttt catgaaagat ggattttct    1380 atttctttca tggaacaaga caatacaaat ttgatcctaa aacgaagaga attttgactc    1440
tccagaaagc taatagctgg ttcaactgca ggaaaaattg aacattacta atttgaatgg    1500
aaaacacatg gtgtgagtcc aagaaggtg tttttcctgaa gaactgtcta ttttctcagt    1560 cattttaac ctctagagtc actgatacac agaatataat cttatttata cctcagtttg    1620
catatttttt tactatttag aatgtagccc ttttttgtact gatataattt agttccacaa    1680
atggtgggta caaaaagtca agtttgtggc ttatggattc atataggcca gagttgcaaa    1740 gatctttttcc agagtatgca actctgacgt tgatcccaga gagcagcttc agtgacaaac    1800
atatcctttc aagacagaaa gagacaggag acatgagtct tgccggagg aaaagcagct    1860 caagaacaca tgtgcagtca ctggtgtcac cctggatagg caagggataa ctcttctaac    1920
acaaaataag tgtttttatgt ttggaataaa gtcaaccttg tttctactgt ttt          1973
```

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4

```
aattaaccct cactaaaggg                                                   20
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
taatacgact cactataggg                                           20

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
aagtggaggg acgtatgca                                            19

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
agctagctca ggatgacatt gatg                                      24

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
gccgatgggc tggacag                                              17

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
tggcgatgga taccccttt                                            19

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
ttctcccaag gtccatagct cat                                       23

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 11
cctgggcaga ttccaaacct                                               20

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
gcaagtcttc cgagtagttt tggat                                         25

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tggcattgct gacatcatga                                               20

<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 14
gccagagggc ccatcaa                                                  17

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
ccccgaagcc tggctaca                                                 18

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
gcatcagctt tgcctgttac t                                             21

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
cgacagtcag ccgcatctt                                                19

<210> SEQ ID NO 18
<211> LENGTH: 18
```

```
<212> TYPE: DNA
<213> ORGANISM: Artificial Sequence
<220> FEATURE:
<223> OTHER INFORMATION: Synthetic oligonucleotide

<400> SEQUENCE: 18
ccccatggtg tctgagcg                                              18

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
tatcatggcc gacaagcaga agaac                                      25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
tttgctcagg gcggactggg tgctc                                      25
```

COMPOSITIONS AND METHODS FOR INHIBITING THE SYNTHESIS OR EXPRESSION OF MMP-1

This application claims benefit of priority under 35 U.S.C. §119 to U.S. Provisional Patent Application Ser. Nos. 60/580,181, filed on Jun. 16, 2004 and 60/645,206, filed on Jan. 20, 2005, whose contents are incorporated herein by reference in their entireties.

This invention was made in the course of research sponsored by the Department of Defense (Grant No. 536338) and the National Institutes of Health (Grant Nos. AR-26599 and CA-77267). The U.S. government may have certain rights in this invention.

BACKGROUND OF THE INVENTION

Matrix metalloproteinases (MMPs) are a family of at least 15 enzymes that degrade the extracellular matrix (ECM) (Borden and Heller (1997) *Crit. Rev. Eukaryotic Gene Expr.* 7:159-178). These enzymes have essential roles in modeling and remodeling the ECM in normal physiology and disease pathology. Several of these enzymes have the unique ability to degrade the interstitial collagens (types I, II, and III), the body's most abundant proteins. MMP-1 is the most ubiquitously expressed interstitial collagenase, thereby assigning it a prominent role in collagen degradation.

Overexpression of MMP-1 is associated with several pathological conditions, including the irreversible degradation of cartilage, tendon, and bone in arthritis (Vincenti, et al. (1996) *Crit. Rev. Eukaryotic Gene Expr.* 6:391-411) and the degradation of collagens I and III in tumor invasion and metastasis (Chambers and Matrisian (1997) *J. Nat'l Cancer Inst.* 89:1260-1270; Murray, et al. (1996) *Nat. Med.* 2:461-462). Patients with tumors that express MMP-1 have an overall poorer prognosis than patients with tumors that do not express this protein (Murray, et al. (1996) supra; Murray, et al. (1998) *J. Pathol.* 185:256-261).

This overexpression of MMP-1 has been suggested to be due to the juxtaposition of transcription factor binding sites within the promoter of this gene and to the cooperativity among the factors that bind these sites (Buttice, et al. (1996) *Oncogene* 13:2297-2306; Basuyaux, et al. (1997) *J. Biol. Chem.* 272:26188-26195; Gutman and Waslyk (1990) *EMBO J.* 9:2241-2246; Benbow and Brinckerhoff (1997) *Matrix Biol.* 15:519-526).

Most normal cells express modest, but detectable, levels of MMP-1 constitutively, and this expression increases substantially in the presence of cytokines or growth factors (Vincenti, et al. (1996) *Crit. Rev. Eukaryotic Gene Expr.* 6:391-411; Rutter, et al. (1997) *J. Cell Biochem.* 66:322-336; Aho, et al. (1997) *Eur. J. Biochem.* 247:503-510; Delany and Brinckerhoff (1992) *J. Cell Biochem.* 50:400-410).

A ~770 nucleotide antisense RNA molecule capable of silencing MMP-1 expression was found to decrease MMP-1 expression in melanoma cells and block in vitro invasion of a collagen matrix (Durko, et al. (1997) *Biochim. Biophys. Acta* 1356:271-80). Using this same antisense RNA molecule, MMP-1 protein expression and enzyme activity were decreased in chondrosarcoma cells and these cells demonstrated a significant decrease in their ability to invade a collagen I barrier (Jiang, et al. (2003) *J. Orthop. Res.* 21(6):1063-70).

SUMMARY OF THE INVENTION

The present invention generally relates to agents which specifically inhibit the synthesis or expression of matrix metalloproteinase 1 (MMP-1) and the use thereof.

One embodiment of the present invention is a method for inhibiting the synthesis or expression of MMP-1 by contacting a cell expressing MMP-1 with an agent that has a sequence complementary to at least part of an MMP-1 nucleic acid sequence. In particular, such an agent encompasses antisense oligonucleotides and siRNA specific to MMP-1 nucleic acid sequences. Specifically, an siRNA encompasses SEQ ID NO:1 and SEQ ID NO:2.

Another embodiment of the present invention is a method for suppressing invasion or metastasis of a tumor cell. This method involves contacting a tumor cell expressing MMP-1 with a sufficient amount of an agent that specifically inhibits the synthesis or expression of the MMP-1. In particular, such an agent encompasses antisense oligonucleotides and siRNA specific to MMP-1 nucleic acid sequences. Specifically, an siRNA encompasses SEQ ID NO:1 and SEQ ID NO:2.

A further embodiment of the present invention is a method of treating, preventing or managing cancer. This method of the invention involves administering to a patient in need of such treatment, prevention or management of cancer a therapeutically or prophylactically effective amount of an agent that inhibits the synthesis or expression of MMP-1. In particular, such an agent encompasses antisense oligonucleotides and siRNA specific to MMP-1 nucleic acid sequences. Specifically, an siRNA encompasses SEQ ID NO:1 and SEQ ID NO:2.

Further embodiments of the present invention are compositions and pharmaceutical compositions containing an agent that specifically inhibits the synthesis or expression of MMP-1. In particular, such an agent encompasses an siRNA specific to MMP-1 nucleic acid sequences. Specifically, an siRNA encompasses SEQ ID NO:1 and SEQ ID NO:2.

The present invention is also a method for detecting the activity of a collagenase. This method involves the steps of suspending a collagenase or cell expressing a collagenase in a solution of collagen, allowing the solution of collagen to solidify, overlaying the solidified collagen with a specified amount of buffer, allowing the collagenase to degrade the collagen, removing the overlayed buffer, and measuring the amount of buffer or collagen in the buffer thereby detecting the activity of the collagenase. In one embodiment, an inhibitory agent is also suspended in the solution of collagen.

DETAILED DESCRIPTION OF THE INVENTION

It has now been shown that the expression of a MMP-1-specific small hairpin RNAs (shRNA) molecule in a breast cancer cell can significantly reduce the expression of MMP-1 mRNA and protein in said cell, block the destruction of collagen matrix, and decrease tumor formation and size.

Therefore, one embodiment of this invention is a method for inhibiting the synthesis or expression of MMP-1 by contacting a cell expressing MMP-1 with an agent that has a sequence complementary to at least part of a MMP-1 nucleic acid sequence. Without being limited by theory, the inhibition is achieved through selectively targeting MMP-1 DNA or mRNA, i.e., by impeding any steps in the replication, transcription, splicing or translation of the MMP-1 gene. The sequence of MMP-1 is well-known in the art and disclosed herein as SEQ ID NO:3 and in GENBANK Accession Nos. NT_033899 and NM_002421, and in Brinckerhoff, et al. ((1987) *J. Clin. Invest.* 79(2): 542-546).

To inhibit the synthesis or expression of MMP-1 means impeding, slowing or preventing one or more steps by which the end-product protein encoded by the MMP-1 gene is synthesized. Typically, the inhibition involves blocking one or more steps in the gene's replication, transcription, splicing or translation through the recognition of a target site located within the gene sequence based on sequence complementation. In a specific embodiment, inhibition of MMP-1 reduces the amount of MMP-1 protein in a cell by greater than about 20, 50, or 80 percent. The amount of MMP-1 can be determined by well-known methods including, but are not limited to, northern blot analysis, RT-PCR, densitometry, fluorometry, radiography, luminometry, antibody-based methods and activity measurements, e.g., in accord with the collagen destruction assay of the instant invention.

An agent that has a sequence that is complementary to at least part of MMP-1 nucleic acid sequence is intended to include an agent that is able to bind to a MMP-1 nucleic acid in a cellular environment in a manner sufficient to disrupt the function (e.g., replication, splicing, transcription or translation) of MMP-1. Generally, such agents bind to the strand of DNA that codes for the MMP-1 amino acid sequence. The binding can result from interactions such as, but not limited to, nucleotide base parings (e.g., A-T/G-C). Such agents can bind to a part or portion of an MMP-1 nucleic acid, e.g., at least 15, 20, or 25 nucleotides, or more generally in the range of 15 to 150 nucleotides.

In particular embodiments of the invention, a sequence is complementary when it hybridizes to its target sequence under stringent conditions. In general, for complementary sequences to hybridize under stringent conditions, said sequences are at least 60, 70, 80, or 90 percent identical to each other. Such stringent conditions are known to those skilled in the art, and can be found, for example, in Current Protocols in Molecular Biology, John Wiley & Sons, N.Y. (1989), 6.3.1-6.3.6. Another example of stringent hybridization conditions is hybridization of the nucleotide in 6x sodium chloride/sodium citrate (SSC) at about 45° C., followed by 0.2xSSC, 0.1% SDS at 50-65° C. Another example of stringent hybridization conditions is hybridization in 6x sodium chloride/sodium citrate (SSC) at about 45° C., followed by one or more washes in 0.2xSSC, 0.1% SDS at 55° C. A further example of stringent hybridization conditions is hybridization in 6x sodium chloride/sodium citrate (SSC) at about 45° C., followed by one or more washes in 0.2xSSC, 0.1% SDS at 60° C. Alternatively, a stringent hybridization condition is hybridization in 6x sodium chloride/sodium citrate (SSC) at about 45° C., followed by one or more washes in 0.2xSSC, 0.1% SDS at 65° C. Another alternative example of stringent hybridization condition is 0.5 M sodium phosphate, 7% SDS at 65° C., followed by one or more washes at 0.2x SSC, 1% SDS at 65° C.

Depending on the conditions under which binding is sufficient to disrupt the function of the MMP-1 gene, a sequence complementary to a target sequence within the MMP-1 nucleic acid sequences need not be 100 percent identical to the target sequence. For example, a sequence can be complementary to its target sequence when at least about 70, 80, 90, or 95 percent of its nucleotides bind via matched base pairings with nucleotides of the target sequence. However, in the present invention it is desirable to achieve MMP-1-specific binding; therefore, a sequence complementary to a target sequence should have limited complementary with other MMPs, e.g., MMP-2, MMP-3, MMP-7 to MMP-28. Sequence complementarity and specificity can be determined empirically using standard methods such as sequence comparisons (e.g., BLAST, DIALIGN, CLUSTALW) or experimentally (e.g., Southern blot analysis under stringent conditions).

The expression of MMP-1 can be inhibited using any well-known method that targets the MMP-1 gene or its mRNA. These methods include, but are not limited to, the use of antisense oligonucleotides, ribozymes, nucleic acids molecules that promote triple helix formation, and siRNAs or co-repression of a target gene by introducing a homologous gene fragment into the cell that harbors the target gene. In particular embodiments, the methods of the present invention employ siRNAs.

In one embodiment, the expression of MMP-1 is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA. See, e.g., Hammond, et al. (2001) *Nature Rev. Gen.* 2:110-119; Sharp (2001) *Genes Dev.* 15:485-490.

Methods and procedures for successful use of RNAi technology are well-known in the art, and have been described in, for example, Waterhouse, et al. (1998) *Proc. Natl. Acad. Sci. USA* 95(23):13959-13964. An MMP-1 short interfering RNA (siRNA) denotes a small interfering RNA that has a sequence complementary to a sequence within the MMP-1 gene. Typically, siRNAs are about 20 to 23 nucleotides in length. The MMP-1 target sequence that binds the siRNA can be selected experimentally or empirically. For example, empirical observations have indicated that shRNA oligonucleotides targeting the transcriptional start site of the target gene (Hannon (2002) *Nature* 418:244-51) or targeting the 3' untranslated region of the mRNA (He and Hannon (2004) *Nature* 5:522-531) are more effective at blocking gene expression. Further, siRNA target sites in a gene of interest are selected by identifying an AA dinucleotide sequence, typically in the coding region, and not near the start codon (within 75 bases) as these may be richer in regulatory protein binding sites which can interfere with binding of the siRNA (see, e.g., Elbashir, et al. (2001) *Nature* 411: 494-498). The subsequent 19-27 nucleotides 3' of the AA dinucleotide can be included in the target site and generally have a G/C content of 30-50%.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using *E. coli* RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp, et al. (2002) *Science* 296(5567): 550-3; Lee, et al. (2002) *Nat. Biotechnol.* 20(5):500-5; Miyagashi and Taira (2002) *Nat. Biotechnol.* 20(5):497-500; Paddison, et al. (2002) *Proc. Natl. Acad. Sci. USA* 99(3):1443-8; Paul, et al. (2002); and Sui, et al. (2002) *Proc. Natl. Acad. Sci.*

USA 99 (8):5515-20. Various methods for introducing such vectors into cells, either in vitro or in vivo (e.g., gene therapy) are known in the art.

Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

The siRNAs of the invention encompass any siRNA that can modulate the selective degradation of MMP-1 mRNA. The siRNAs of the invention include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the action of one or more endogenous degradative enzymes.

An exemplary siRNA that can be used to inhibit the expression of MMP-1 is the shRNA described herein as SEQ ID NO:1 (sense strand) and SEQ ID NO:2 (antisense strand). However, as would be understood by one of skill in the art, any nucleic acid target sequence in MMP-1, which is unique to MMP-1 and not found in other MMP sequences, can be used to carry out the methods of the present invention.

In another embodiment, the agent for use in the methods of the present invention is an oligonucleotide which is antisense to MMP-1 coding sequences. An antisense oligonucleotide refers to an oligonucleotide having a sequence complementary to the coding strand of a MMP-1 nucleic acid (e.g., DNA or RNA sequence). Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site, impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins.

Antisense oligonucleotides of the invention include oligonucleotides having modified sugar-phosphodiester backbones or other sugar linkages, which can provide stability against endonuclease attacks. The invention also encompasses antisense oligonucleotides that are covalently attached to an organic or other moiety that increases their affinity for a target nucleic acid sequence. Agents such as, but not limited to, intercalating agents, alkylating agents, and metal complexes can be also attached to the antisense oligonucleotides of the invention to modify their binding specificities.

In particular embodiments, an antisense oligonucleotide is a cDNA that, when introduced into a cell, transcribes into an RNA molecule having a sequence complementary to at least part of the MMP-1 mRNA. Such target sequences can be based on all or part of SEQ ID NO:1 or other sequences specific to MMP-1.

In alternative embodiments, other nucleic acid-based agents can be used in the carrying out the methods of the present invention. Ribozymes are enzymatic RNA molecules capable of catalyzing the specific cleavage of RNA. The characteristics of ribozymes are well-known in the art. See, e.g., Rossi (1994) *Current Biology* 4:469-471. Without being limited by theory, the mechanism of ribozyme action involves sequence-specific hybridization of the ribozyme molecule to complementary target RNA, followed by an endonucleolytic cleavage. The composition of ribozyme molecules should include one or more sequences complementary to the target gene mRNA, and should include the well-known catalytic sequence responsible for mRNA cleavage, which is disclosed in U.S. Pat. No. 5,093,246, incorporated herein by reference in its entirety. If the sequence of a target mRNA is known, a restriction enzyme-like ribozyme can be prepared using standard techniques.

The expression of the MMP-1 gene can also be inhibited by using triple helix formation. Nucleic acid molecules to be used in triple helix formation for the inhibition of transcription should be single-stranded and composed of deoxynucleotides. The base composition of these oligonucleotides should be designed to promote triple helix formation via Hoogsteen base paring rules, which generally require sizeable stretches of either purines or pyrimidines to be present on one strand of a duplex. Nucleotide sequences can be pyrimidine-based, which will result in TAT and CGC$^+$ triplets across the three associated strands of the resulting triple helix. The pyrimidine-rich molecules provide base complementarily to a purine-rich region of a single-strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The expression of MMP-1 can be also inhibited by co-repression. Co-repression refers to the phenomenon in which, when a gene having an identical or similar to the target sequence is introduced to a cell, expression of both introduced and endogenous genes becomes repressed. This phenomenon, although first observed in plant system, has been observed in certain animal systems as well. The sequence of the gene to be introduced does not have to be identical to the target sequence, but sufficient homology allows the co-repression to occur. The determination of the extent of homology depends on individual cases, and is within the ordinary skill in the art.

It would be readily apparent to one of ordinary skill in the art that other methods of gene expression inhibition that selectively target a DNA or mRNA can also be used in connection with the present invention without departing from the essence of the invention.

Having demonstrated that inhibition of MMP-1 expression blocks the destruction of collagen matrix and decreases tumor size, the present invention further relates to a method for suppressing invasion or metastasis of a tumor cell. The method involves contacting a tumor cell with an agent that has a sequence complementary to at least part of the coding strand of MMP-1 nucleic acid sequence so that invasion or metastasis of the tumor cell is suppressed. As used herein, suppression or suppressing, when used in relation to the invasion or metastasis of a tumor cell, is intended to mean retardation or prevention of the growth, invasion or metastasis of the tumor cell. Such suppression can be, but is not necessarily, accomplished by inhibiting the expression of MMP-1 thereby blocking the degradation of the extracellular matrix. In particular embodiments of this invention, invasion or metastasis of a tumor cell is suppressed when the growth, invasion or metastasis is slowed by greater than about 20, 30, 50, 75, 100 or 200 percent as determined by, e.g., the growth of primary or secondary tumors or tumor volume.

Another embodiment of the present invention encompasses a method of treating, preventing or managing cancer comprising administering to a patient in need of such treatment or management a therapeutically or prophylactically effective amount of an agent that inhibits the synthesis or expression of MMP-1 nucleic acid sequences. Such a method can be carried out using an agent that has a sequence complementary to at least part of the MMP-1 nucleic acid sequence (e.g., an antisense oligonucleotide or MMP-1 siRNA). Suitable siRNAs include, but are not limited to, shRNA molecules having a sequence corresponding to SEQ ID NO:1 and SEQ ID NO:2.

As used herein, the term treating cancer or treatment of cancer means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

Preventing cancer or prevention of cancer is intended to mean preventing the occurrence or recurrence of the disease state of cancer. As such, a treatment that impedes, inhibits, or interferes with metastasis, tumor growth, or cancer proliferation is deemed preventive.

As used herein, managing cancer encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

Methods of the invention can be used to treat and manage patients suffering from primary and metastatic cancer. Further encompassed is the treatment of patients who have been previously treated for cancer, as well as those who have not previously been treated for cancer. The invention encompasses first-line, second-line, third-line and further line cancer treatments.

Cancers that can be treated and managed using methods of the invention include but are not limited to, those associated with an increase in the expression of MMP-1, e.g., breast cancer, colorectal cancer, renal cell carcinoma, malignant melanoma, endometriosis, cervical cancer, esophageal, pancreatic, gastric and bladder cancer (Airola, et al. (1999) *Br. J. Cancer* 80:733-43; Inoue, et al. (1999) *Int. J. Mol. Med.* 4:73-7; Ito, et al. (1999) *Mod. Pathol.* 12:669-74; Murray, et al. (1998) *J. Pathol.* 185:256-61; Murray, et al. (1996) *Nat. Med.* 2:461-2; Nakopoulou, et al. (1999) *Hum. Pathol.* 30:436-42). In particular embodiments, the cancer is breast cancer.

It is further contemplated that the agents of the present invention (e.g., antisense oligonucleotides and siRNAs) can be used in the treatment of other diseases or conditions for which MMP-1 has an associated role, e.g., osteoarthritis, ulcerative colitis, early implant failure, inflammatory bowel disease, delayed wound healing, progressive adult-onset emphysema, and heart failure.

It would be readily apparent to one of ordinary skill in the art that the agents of the present invention (e.g., antisense oligonucleotides and siRNAs such as shRNA) can be combined with one or more other anti-cancer therapies. The agents of the invention can be administered simultaneously or sequentially with well-known antineoplastic agents such as antimetabolites, alkylating agents, spindle poisons and/or intercalating agents, and proteins such as interferons.

The determination of the identity and amount of second anti-cancer agent(s) for use in a method of the invention can be readily made by ordinarily skilled medical practitioners using standard techniques known in the art, and will vary depending on the type and severity of cancer being treated.

The agents of the present invention and second anti-cancer agents can be administered simultaneously or sequentially by the same or different routes of administration. The suitability of a particular route of administration employed for a particular agent will depend on the agent itself (e.g., whether it can be administered orally without decomposing prior to entering the blood stream) and the disease being treated. For example, treatment of tumors on the skin or on exposed mucosal tissue may be more effective if one or both active ingredients are administered topically, transdermally or mucosally (e.g., by nasal, sublingual, buccal, rectal, or vaginal administration). Treatment of tumors within the body, or prevention of cancers that may spread from one part of the body to another, may be more effective if one or both of the active ingredients are administered parenterally or orally. Similarly, parenteral administration may be preferred for the acute treatment of a disease, whereas transdermal or subcutaneous routes of administration may be employed for chronic treatment or prevention of a disease. Preferred routes of administration for the anti-cancer agents are known to those of ordinary skill in the art.

The present invention further encompasses pharmaceutical compositions containing an agent that inhibits the synthesis or expression of the MMP-1 gene. In a particular composition, the agent is an oligonucleotide antisense to MMP-1 nucleic acid sequences. Specifically, the oligonucleotide is a cDNA that transcribes into an RNA having a sequence complementary to MMP-1 nucleic acid sequences or is a chemically synthesized antisense oligonucleotide of 15-150 nucleotides in length. In another composition, the agent is a 15-150 nucleotide MMP-1 siRNA such as an shRNA. Suitable siRNAs include, but are not limited to, an shRNA having a sequence corresponding to SEQ ID NO:1 and SEQ ID NO:2.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the invention from degradation within the gastrointestinal tract. In another example, the agents of the invention may be administered in a liposomal formulation to shield the agents from degradative enzymes, facilitate transport in circulatory system, and effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the invention will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

Delivery of the agents of the invention (e.g., antisense oligonucleotides or siRNAs) into a patient can either be direct, i.e., the patient is directly exposed to an agent of the invention or agent-carrying vector, or indirect, i.e., cells are first transformed with the nucleic acid sequences encoding an agent of the invention in vitro, then transplanted into the patient for cell replacement therapy. These two approaches are known as in vivo and ex vivo therapy, respectively.

In the case of in vivo therapy, the agents of the invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector (U.S. Pat. No. 4,980,286, for example), by direct injection of naked DNA, by use of microparticle bombardment (for example, a gene gun; BIOLISTIC®, DuPont), by coating with lipids or cell-surface receptors or transfecting agents, encapsulation in liposomes, microparticles, or microcapsules, by administering them in linkage to a peptide which is known to enter the cell or nucleus, or by administering them in linkage to a ligand subject to receptor-mediated endocytosis (Wu and Wu (1987) J. Biol. Chem. 262:4429-4432), which can be used to target cell types specifically expressing the receptors. Further, the agents of the invention can be targeted in vivo for cell-specific uptake and expression, by targeting a specific receptor, as disclosed in, for example, WO 92/06180, WO 92/22635, WO92/20316, WO93/14188, and WO 93/20221.

Ex vivo therapy involves transferring the agents of the invention to cells in tissue culture by methods such as electroporation, lipofection, calcium phosphate-mediated transfection, and viral infection. Usually, the method of transfer includes the transfer of a selectable marker to the cells. The cells are then placed under selection to isolate those cells that have taken up and are expressing the transferred compounds. Those cells are then delivered to a patient.

The agents of the invention are introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, and spheroplast fusion. Numerous techniques are known in the art for the introduction of foreign compounds into cells. Examples of such techniques are disclosed in Loeffler, et al. (1993) Meth. Enzymol. 217:599-618; Cohen, et al. (1993) Meth. Enzymol. 217:618-644; and Cline (1985) Pharmac. Ther. 29:69-92. These techniques should provide for the stable transfer of the agents of the invention to the cell, so that they are expressible by the cell and preferably heritable and expressible by its cell progeny.

The resulting recombinant cells can be delivered to a patient by various methods known in the art. Examples of the delivery methods include, but are not limited to, subcutaneous injection, skin graft, and intravenous injection.

Pharmaceutical compositions of the invention that are suitable for oral administration can be presented as discrete dosage forms containing predetermined amounts of active ingredients, and may be prepared by methods of pharmacy well-known to those skilled in the art. See generally, Remington: The Science and Practice of Pharmacy, Alfonso R. Gennaro, editor, 20th ed. Lippincott Williams & Wilkins: Philadelphia, Pa., 2000.

Typical oral dosage forms of the invention are prepared by combining the active ingredients in an intimate admixture with at least one pharmaceutically acceptable carrier according to conventional pharmaceutical compounding techniques. Carriers can take a wide variety of forms depending on the form of preparation desired for administration.

Because of their ease of administration, tablets and capsules represent the most advantageous oral dosage unit forms, in which case solid carriers are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Disintegrants or lubricants can be used in pharmaceutical compositions and dosage forms of the invention.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable carrier for injection, suspensions ready for injection, and emulsions.

Suitable carriers that can be used to provide parenteral dosage forms of the invention are well-known to those skilled in the art. Examples include, but are not limited to: Water for Injection USP; aqueous carriers such as, but not limited to, Sodium Chloride Injection, Ringer's Injection, Dextrose Injection, Dextrose and Sodium Chloride Injection, and Lactated Ringer's Injection; water-miscible carriers such as, but not limited to, ethyl alcohol, polyethylene glycol, and polypropylene glycol; and non-aqueous carriers such as, but not limited to, corn oil, cottonseed oil, peanut oil, sesame oil, ethyl oleate, isopropyl myristate, and benzyl benzoate.

Compounds that increase the solubility of one or more of the active ingredients (i.e., the agents of the invention and second anti-cancer agents) disclosed herein can also be incorporated into the parenteral dosage forms of the invention.

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy, Alfonso R. Gennaro, editor, 20th ed. Lippincott Williams & Wilkins: Philadelphia, Pa., 2000; and Introduction to Pharmaceutical Dosage Forms, 4th ed., Lea & Febiger, Philadelphia (1985). Transdermal dosage forms include reservoir type or matrix type patches, which can be applied to the skin and worn for a specific period of time to permit the penetration of a desired amount of active ingredients.

Suitable carriers and other materials that can be used to provide transdermal, topical, and mucosal dosage forms encompassed by this invention are well-known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid carrier for the formulation, as an emulsifying agent or surfactant, and as a delivery-enhancing or penetration-enhancing agent. Different salts, hydrates or solvates of the active ingredients can be used to further adjust the properties of the resulting composition.

The present invention is also a method for detecting the activity of a collagenase. The method involves the steps of suspending a collagenase or cell expressing or suspected of expressing a collagenase in a solution of collagen, allowing the solution of collagen to solidify, overlaying the solidified collagen with a specified amount of buffer, allowing the collagenase to degrade the collagen, removing the overlayed buffer, and measuring the amount of buffer or collagen in the buffer thereby detecting the activity of the collagenase.

As will be appreciated by the skilled artisan, this assay of the instant invention can be used to detect the activity of any collagenase and can incorporate any type of collagen. A collagenase can be purified or a mixture of proteins and can be any protein that has the capacity to degrade collagen. In certain embodiments, the collagenase is an MMP. In particular embodiments, the collagenase is MMP-1. The collagen used in the instant assay will be dependent upon the collagenase activity being detected. Type I collagen is particularly useful, however, Type II to Type XII collagen are also encompassed within the scope of the instant assay.

Type I collagen is the most abundant collagen of the human body. It is present in scar tissue, tendons, and the organic part of bone. Type II collagen is a component of articular cartilage and is found in association with Type IX collagen, whereas Type III collagen is the collagen of granulation tissue, and is produced quickly by young fibroblasts before the tougher type I collagen is synthesized. Type XII collagen is found to interact with types I and III collagen. Type IV collagen is part of the basal lamina. Type V and Type VI collagen are components of most interstitial tissue and are associated with type I collagen. Type VII collagen is a component of the epithelia as is Type VIII collagen. Type X collagen is hypertrophic and part of mineralizing cartilage, whereas Type XI collagen is a component of cartilage. Therefore, particular collagenases which specifically target any one of these types of collagens can be detected in the assay of the invention. In one embodiment, the assay is used to monitor the degradation of a collagen of interstitial tissue. In a particular embodiment, the assay is used to monitor the degradation of a type I collagen.

Advantageously, collagen can be obtained in solution as a pepsin-solubilized collagen dissolved in acid (e.g., Vitrogen; ANGIOTECH® Biomaterials, Palo Alto, Calif.). Upon neutralization (e.g., to pH 7.0 to pH 7.4 with NaOH), a collagenase or cell expressing or suspected of expressing a collagenase is suspended in the solution of collagen and the collagen is allowed to solidify via fibrillogenesis (e.g., at 24° C. to 37° C. in the presence or absence of $CO_2$) with the collagenase or cells suspended therein.

Subsequently, the solidified collagen is overlayed with a specified amount of buffer. A specified amount of buffer means that the volume, weight, or mass of the buffer being used is a measured amount. By allowing the collagenase to degrade the collagen, e.g., for 30 minutes to 5 days, buffer and collagen fragments are released from the collagen matrix. To detect the activity of the collagen, the overlayed buffer is removed and the amount of collagen fragments in the buffer and/or the amount of buffer released is measured. Because some cells (e.g., fibroblasts) can contract collagen thereby releasing buffer without collagen degradation, it may be advantageous to measure both the amount of collagen fragments in the buffer and the amount of buffer released. MDA-231 cells exemplified herein did not contract collagen and therefore the amount of buffer released was a result of collagenase activity. The amount of collagen fragments released can be measured via ELISA or any other suitable assay. The amount of buffer released can be determined by measuring the volume, weight, or mass of the buffer removed from the solidified collagen. The collagenase activity detected can be expressed as present or absent; expressed in terms of activity as compared to a control amount of collagenase, such as that found in a standard curve; or expressed as a value based upon the weight, volume or mass of buffer released or the amount of collagen released into the buffer.

As disclosed herein, the collagenase destruction assay of the instant invention is useful in the analysis of inhibitors that decrease or block the expression (e.g., siRNA) or activity (e.g., aprotinin) of a collagenase. Accordingly, one embodiment of the instant assay is the use of an inhibitory agent suspended in the solution of collagen. The inhibitory agent can be a known collagenase inhibitor (e.g., aprotinin) or part of a library of chemical compounds which is being screened for collagenase inhibitor activity. Such a library of chemical compounds can encompass numerous chemical classes, though typically they are organic molecules, preferably small organic compounds having a molecular weight of more than 100 and less than about 2,500 daltons. Libraries of such compounds can contain either collections of pure agents or collections of agent mixtures. Examples of pure agents include, but are not limited to, proteins, antibodies, peptides, peptide aptamers, nucleic acids, oligonucleotides, carbohydrates, lipids, synthetic or semi-synthetic chemicals, and purified natural products. Such libraries are commercially available to the skilled artisan. Examples of agent mixtures include, but are not limited to, extracts of prokaryotic or eukaryotic cells and tissues, as well as fermentation broths and cell or tissue culture supernates. As such, the collagenase destruction assay of the instant invention can be used in high throughput assays for the identification of collagenase inhibitors.

Moreover, the collagenase destruction assay can be used to analyze the effect of substitutions, deletions, and other mutations on collagenase activity in a cell.

The invention is described in greater detail by the following non-limiting examples.

EXAMPLE 1

Material and Methods

Cell Culture. NIH/3T3 cells from American Type Culture Collection (ATCC) were cultured in Dulbecco's modified Eagle's medium (DMEM) containing 10% fetal calf serum (FCS), penicillin/streptomycin (100 U/mL and 100 µg/mL), and glutamine (2 mM). MDA-231 cells (ATCC) were cultured in DMEM/F12 50:50 media with 10% FCS, penicillin/streptomycin (100 U/mL and 100 µg/mL), and glutamine (2 mM). For experiments, cultures of MDA-231 cells were washed three times in Hank's balanced salt solution (HBSS) to remove traces of serum and then placed in serum-free medium.

MMP-1 and eGFP Expression Plasmids. The pCMV-MMP-1 expression construct was prepared using standard techniques. NotI and SalI restriction enzymes (INVITROGEN™, Carlsbad, Calif.) were used to excise the complete MMP-1 cDNA from pSP64-MMP-1 (ATCC), and to digest the pCMV-Tag4c vector (STRATAGENE®, La Jolla, Calif.). Digestion products were purified on agarose gels and the MMP-1 cDNA fragment was ligated into the pCMV-Tag 4c vector to create the pCMV-MMP-1 vector. The enhanced GFP expression vector (peGFP) is commercially available from BD Biosciences (San Jose, Calif.).

shRNA Expression Plasmids. Circular pSuper vectors (PSUPER™ and PSUPER™.Retro.Neo.GFP; OLIGOENGINE™, Seattle, Wash.) were linearized with BglII and HindIII restriction enzymes (INVITROGEN™, Carlsbad, Calif.), and dephosphorylated with calf intestinal phosphatase (cip; GIBCO®, Gaithersburg Md.). DNA oligonucleotides specifically designed for use with the PSUPER™ plasmids, and containing either MMP-1 shRNA sequence or scrambled shRNA sequence were annealed to create double-stranded oligonucleotides to be cloned into the PSUPER™ vectors. Annealed oligonucleotides were phosphorylated with T4 polynucleotide kinase (PROMEGA®, Madison, Wis.), and ligated to the PSUPER™ plasmids, and then transformed into bacteria. The newly created PSUPER™-MMP-1 shRNA, PSUPER™ retro-MMP-1 shRNA, and PSUPER™ retro-scrambled shRNA vectors were prepared from individual bacterial colonies. Correct orientation and location of the oligonucleotide cloning were confirmed by sequencing the plasmids with T3 and T7 primers (T3,5'-AAT TAA CCC TCA CTA AAG GG-3', SEQ ID NO:4; T7, 5'-TAA TAC GAC TCA CTA TAG GG-3', SEQ ID NO:5), and the BIGDYE™ sequencing reagent (APPLIED BIOSYSTEMS™, Foster City, Calif.). MMP-1 shRNA oligonucleotides (MMP-1 sense 5'-GAT CCC C<u>ACCAGATGCTGAAACCCTGT TCA AGA GA<u>CAGGGTTTCAGCATCTGGT</u> TTT TTG GAA A-3', SEQ ID NO:1; MMP-1 antisense 5'-AGC TTT TCC AAA AA<u>ACCAGATGCTGAAACCCTG</u> TCT CTT GAA <u>CAGGGTTTCAGCATCTGGTGG</u> G-3', SEQ ID NO:2) contained a region specific to bases 234-252 of MMP-1 mRNA (underlined) a hairpin loop region (italic), and 5' and 3' linker sequences for subcloning into the BglII and HindIII sites of the PSUPER™ vectors. The scrambled shRNA oligonucleotides contained identical hairpin loop and linker sequence, but contained a sequence of DNA that was not complimentary to any human gene (AA GTG GAG GGA CGT ATG CA; SEQ ID NO:6).

Transfection of NIH/3T3 and MDA-231 Cells. NIH/3T3 cells were transiently transfected with LIPOFECTAMINE™ 2000 (INVITROGEN™, Carlsbad, Calif.) along with 0.5 µg peGFP, 0.5 µg pCMV-MMP-1, and 2 µg PSUPER™-MMP-1 shRNA or PSUPER™ with no insert. Transfection efficiency was monitored using eGFP signal. Total cellular RNA was harvested 48 hours after transfection and analyzed for MMP-1 mRNA by real-time RT-PCR. MDA-231 cells were stably transfected in triplicate with LIPOFECTAMINE™ 2000 (INVITROGEN™, Carlsbad, Calif.) and 2 µg of the PSUPER™.Retro.Neo.GFP plasmid containing the MMP-1 shRNA, the scrambled sequence or just the empty vector. Stable cell lines were selected by growth in the presence of 1 mg/mL G418 (STRATAGENE®, La Jolla, Calif.). Individual, stable cell lines were isolated with cloning disks according to the manufacturer's instructions (PGC Scientifics, Frederick, Md.).

RNA Isolation and Real-Time RT-PCR. MDA-231 stable cell lines cultured in serum-free medium for 24 hours were trypsinized and pelleted. RNA was harvested using the RNEASY® RNA isolation kit (QIAGEN®, Valencia, Calif.) and DNA contamination was removed from the RNA samples with RNase-free DNase (QIAGEN®, Valencia, Calif.). For real-time RT-PCR, reverse transcription (RT) was performed using protocols and reagents from APPLIED BIOSYSTEMS™ TAQMAN® reverse transcription reagent kit. Briefly, 2 µg of DNase-treated RNA were reverse transcribed in a 20 µL reaction containing 5.5 mM $MgCl_2$, 500 µM each dNTP, 2.5 µM oligo $d(T)_{16}$, 0.4 U/µL RNase inhibitor, and 1.25 U/µL MULTISCRIBE™ reverse transcriptase. The reactions were incubated at 25° C. for 5 minutes, 48° C. for 30 minutes, and 95° C. for 5 minutes.

Real-time PCR was performed with reagents and protocols from the APPLIED BIOSYSTEMS™ SYBR® Green master mix kit. Five µL of each RT reaction were used to amplify MMP cDNA in triplicate real-time PCR reactions and 2 µL of each RT reaction were used to amplify GAPDH or eGFP cDNA in duplicate reactions. To enable quantitative comparisons between PCR assays, standard curves were generated with every assay. The PCR reactions contained 200 nM of each primer and were incubated on an MJ Research OPTICON™ real-time detection thermal cycler at 95° C. for 10 minutes, followed by 50 PCR cycles of 950 for 15 seconds, and 60° C. for 1 minute, and a plate read. The PCR cycles were followed by a SYBR® green melting curve from 55° C. to 90° C. MMP mRNA levels are reported as copies of the target gene/pg GAPDH or eGFP.

Real-Time PCR Primer Sequences. The MMP-2 and MMP-9 primer were generated from well-known sequences. The remaining primers were designed using OLIGO® primer analysis software (Molecular Biology Insights, Cascade, Colo.). Forward (F) and reverse (R) real-time PCR primers for MMP-1, MMP-2, MMP-9, MMP-14 (MT1-MMP), GAPDH, and peGFP were: MMP-1 forward 5'-AGC TAG CTC AGG ATG ACA TTG ACA ATG-3', SEQ ID NO:7; MMP-1 reverse 5'-GCC GAT GGG CTG GAC AG-3', SEQ ID NO:8; MMP-2 forward 5'-TGG CGA TGG ATA CCC CTT T-3', SEQ ID NO:9; MMP-2 reverse 5'-TTC TCC CAA GGT CCA TAG CTC AT-3', SEQ ID NO:10; MMP-9 forward 5'-CCT GGG CAG ATT CCA AAC CT-3', SEQ ID NO:11; MMP-9 reverse 5'-GCA AGT CTT CCG AGT AGT TTT GGA T-3', SEQ ID NO:12; MMP-13 forward 5'-TGG CAT TGC TGA CAT CAT GA-3', SEQ ID NO:13; MMP-13 reverse 5'-GCC AGA GGG CCC ATC AA-3', SEQ ID NO:14; MMP-14 forward 5'-CCC CGA AGC CTG GCT ACA-3', SEQ ID NO:15; MMP-14 reverse 5'-GCA TCA GCT TTG CCT GTT ACT-3', SEQ ID NO:16; GAPDH forward 5'-CGA CAG TCA GCC GCA TCT T-3', SEQ ID NO:17; GAPDH reverse 5'-CCC CAT GGT GTC TGA GCG-3', SEQ ID NO:18; eGFP forward 5'-TAT CAT GGC CGA CAA GCA GAA GAA C-3', SEQ ID NO:19; eGFP reverse 5'-TTT GCT CAG GGC GGA CTG GGT GCT C-3', SEQ ID NO:20.

Real-Time PCR Standards. The real-time standards for MMP-1, MMP-2, MMP-9, GAPDH, and peGFP were plasmids containing either a portion or all of the cDNA of the target gene. The standard for MMP-14 was a PCR fragment generated with the real-time primers. Plasmid dilutions for standards were serial log dilutions from 1 ng to 10 fg, The MMP-14 standards were diluted from 10 pg to 1 fg. Numbers for converting pg to copies of mRNA were 360,000 copies/pg MMP-1, 480,000 copies/pg MMP-2, 340,000 copies/pg MMP-9, 270,000 copies/pg MMP-13, and $10 \times 10^6$ copies/pg MMP-14 (MT1-MMP).

Interferon Response RT-PCR Assay. RNA pooled from MDA-231 ells containing empty vector or the MMP-1 shRNA were reverse-transcribed with M-MLV reverse transcriptase (INVITROGEN™) according to the manufacturer's instructions. Briefly, 3 µg of RNA, 99 ng random hexamers, and 10 nmoles of dNTP were combined to a total volume of 12 µL. The mixture was incubated at 65° C. for 5 minutes and cooled to 4° C. Four µL of 5× reverse strand buffer, 2 µL of 0.1 M DTT, and 1 µL of RNase inhibitor A (40 U/µL) were then added to the reaction and it was incubated at 37° C. for 2 minutes. One µL of M-MLV reverse transcriptase was added to the reaction and incubated at 25° C. for 10 minutes, 37° C. for 50 minutes and 70° C. for 15 minutes. The expression levels of 11 interferon-responsive genes and GAPDH were then estimated using semi-quantitative PCR and the human interferon-response MULTIGENE-12™ RT-PCR Profiling Kit (SuperArray Bioscience Co., Frederick, Md.).

ELISA for MMP-1 Protein. MMP-1 protein in serum-free culture medium of stably transfected MDA-231 cells was quantified with the human MMP-1 BIOTRAK™ ELISA system that measures both latent and active enzyme (Amersham). Cells were grown in six-well culture dishes with 1 mL of serum-free medium, and after 24 hours of incubation, 100 µL of a 1:30 dilution of the medium was used for the ELISA assays. The cells remaining in the wells were lysed with 350 µL passive lysis buffer (PROMEGA®, Madison, Wis.), and 70 µl was used in a Bradford assay (BIO-RAD®, Hercules, Calif.) to determine the total protein content. The ng of MMP-1 protein from the ELISA results was normalized to µg total protein.

Western Blot Analysis. MDA-231 cells were cultured in 1 mL serum-free DMEM/F12 medium in six-well plates in the presence or absence of a collagen gel, with or without aprotinin (50 U/mL; Sigma, St. Louis, Mo.). After 24 hours, medium was harvested, proteins precipitated with cold 10% trichloroacetic acid, and resuspended in 50 µL SDS loading buffer (PROMEGA®, Madison, Wis.). Following SDS-PAGE and transfer to a PVDF membrane (IMMOBILON™-P; MILLIPORE™, Bedford, Mass.), the membrane was incubated in a 5% milk, Tris-buffered saline solution with 0.1% TWEEN™ (milk TBST) for 1 hour. The membrane was probed with a MMP-1 polyclonal antibody (CHEMICON®, Temecula, Calif.) diluted 1:5000 in milk TBST overnight at 4° C. The membrane washed three times with TBST, and a 1:2000 dilution of goat anti-rabbit horseradish peroxidase (HRP) conjugated antibody (CELL SIGNALING TECHNOLOGY®, Beverly, Mass.) in milk TBST was added for 60 minutes. The blot washed three times with TBST, and HRP activity was detected with the WESTERN LIGHTNING® chemiluminescence reagent according to the manufacturer's instructions (PERKINELMER®, Boston, Mass.).

Cell Proliferation Assay. The proliferation rate of the stably transfected MDA-231 cell lines at 24 and 48 hours was determined with a MTT assay as described in the manufacturer's protocol (ATCC). The optimum cell count was 10,000 cells per well of a 96-well tissue culture dish.

In vitro Collagen Gel Destruction Assay. Collagen preparations were carried out on ice to prevent premature jelling. A solution of purified type I bovine collagen (Cohesion Technologies, Palo Alto, Calif.) was neutralized with a sterile 10× phosphate-buffered saline (pH 7.4), and 0.1 M NaOH. The solution of neutralized collagen (2 mg/mL) was mixed with an equivalent volume of cells suspended in serum free DMEM to yield a final concentration of $2 \times 10^5$ cells/mL in 1 mg/mL fibrillar collagen, and 1 mL of the collagen/cell mixture was added to each well of a six-well plate. After approximately 1 hour, the collagen jelled, and 1 mL of serum-free media was added on top of the gel. For some experiments, 25 µM ILOMASTAT® (CHEMICON®, Temecula, Calif.), 50 U/mL aprotinin (Sigma, St. Louis, Mo.), 1 ug/mL neutralizing MMP-1 antibody (MMP-1 ab-5; ONCOGENE™ Research Products, San Diego, Calif.), 1 µg/mL monoclonal FLAG® antibody (Sigma, St. Louis, Mo.), or 1% DMSO were added to the collagen before it jelled. After 36 hours of incubation at 37° C. the medium was removed from the top of collagen gels and weighed. The weight of media added at the start of the 37° C. incubation (1 gram) was subtracted from the total media weights to reveal the amount of media liberated by collagen gel destruction.

Tumorigenesis Studies in Mice. Pooled MDA-231 stable cell lines containing either the empty vector or the MMP-1 shRNA ($1 \times 10^6$ cells/100 µL HBSS) were injected into the $4^{th}$ inguinal fat pad of twenty-one female, 6-week-old nude mice (NU/NU; Charles River Laboratories, Wilmington, Mass.) using 28 gauge×½" single-use insulin needles. Mice were examined weekly until tumors were grossly apparent, then they were examined several times per week. Each tumor was measured twice with Vernier calipers, and tumor volume was calculated using the formula: $4/3\pi r^3$. When the two measurements differed, the smaller radius measurement was squared and multiplied by the largest radius measurement. This number was then substituted for the $r^3$ portion of the formula.

Statistical Methods. Two different statistical tests were utilized to calculate statistical differences. Student's t-test was used to calculate the statistical significance of measurements of MMP levels, collagen destruction, cell proliferation, and tumor size. Fisher's exact test was utilized to determine whether there was a correlation between tumor incidence and the presence of MMP-1 shRNA.

EXAMPLE 2

MMP-1 shRNA Design

The shRNA sequence was homologous to only MMP-1 mRNA as confirmed with NCBI's BLAST search engine. Since RNAi is thought to be a cytoplasmic process, the shRNA selected was complementary to an exonic sequence of the mRNA (Dykxhoorn, et al. (2003) *Nat. Rev. Mol. Cell Biol.* 4:457-67; Tuschl (2002) *Nat. Biotech.* 20:446-8). Additional design considerations made the shRNA sequence compatible with the PSUPER™ plasmid-based systems for shRNA expression. These plasmids contain an H1 RNA polymerase III promoter that requires an adenine at the +1 nucleotide position. Tangent thymine residues were avoided because four or more thymine residues in a row are the termination sequence for the H1 RNA polymerase (Brummelkamp, et al. (2002) supra).

EXAMPLE 3

Inhibition of MMP-1 with siRNA

To test the efficacy of the shRNA inhibition of MMP-1 expression, shRNA composed of SEQ ID NO:1 and SEQ ID NO:2 was cloned it into the PSUPER™ shRNA vector. Two PSUPER™ plasmids were used; one with the MMP-1 shRNA sequence to block MMP-1 gene expression, and one with only the plasmid vector. NIH/3T3 mouse embryonic fibroblasts were used as the model cell line because they do not contain a homolog to MMP-1, and because they are easily transfectable. MMP-1 mRNA production was supplied to the NIH/3T3 cells by a plasmid producing the mRNA from a CMV promoter (pCMV-MMP-1-tag), and transfection efficiency was tracked by co-transfection with an enhanced GFP plasmid (peGFP). The enhanced GFP mRNA expressed by the cells was also used as a control gene to normalize the MMP-1 mRNA levels. Forty-eight hours after transfection, MMP-1 mRNA levels of cells transfected with the MMP-1 shRNA vector were 73% lower than the MMP-1 levels of cells transfected with the empty vector (P=0.015). These data indicated that the MMP-1 shRNA effectively reduced MMP-1 mRNA levels; consequently, the shRNA oligonucleotides were cloned into the stably integrating PSUPER™-retro plasmid to create MDA-231 cell lines.

Three groups of stable MDA-231 cell lines were created. One group contained only the PSUPER™-retro plasmid, a second group contained a PSUPER™-retro plasmid with the scrambled shRNA sequence, and the third contained a PSUPER™-retro plasmid with the MMP-1 shRNA oligonucleotide. Cells with the scrambled shRNA did not grow well, and did not survive the subcloning procedures. Analysis of the shRNA sequence using NCBI's BLAST search did not reveal any homology to mammalian genes.

After initial neomycin selection and isolation of individual stable cell lines, MMP-1 mRNA and protein levels were determined using quantitative RT-PCR (qRT-PCR) and ELISA. MMP-1 mRNA levels were measured in RNA harvested from stably transfected cell lines after a 24 hour incubation in serum-free medium and were normalized to GAPDH mRNA levels. MMP-1 protein levels were measured in the serum-free media of the cell lines after 24 hours of incubation and were normalized to total protein content of the cells. The ELISA measured total (active and zymogen) forms of MMP-1 protein. Three cell lines producing MMP-1 shRNA had a greater than 90% reduction in MMP-1 mRNA and protein levels when compared to the cell lines containing the empty vector cells (Table 1). To control for differences introduced into the cell lines during selection, these three individual cell lines for each group were pooled, and all subsequent experiments were performed on pooled cells.

TABLE 1

| PSUPER ™ retro insert | MDA-231 Cell Line # | Copies of MMP-1 mRNA per pg GAPDH mRNA | ng of MMP-1 protein per µg of total protein |
|---|---|---|---|
| Empty Vector | A1 | 380,000 ± 210,000 | 19.10 ± 6.67 |
|  | A11 | 550,000 ± 320,000 | 30.70 ± 6.94 |
|  | A12 | 680,000 ± 230,000 | 24.63 ± 7.26 |
|  | Group | 540,000 ± 260,000 | 24.81 ± 5.81 |
| MMP-1 shRNA | D1 | 8900 ± 3600 | 0.49 ± 0.03 |
|  | Y2 | 4600 ± 2500 | 0.47 ± 0.01 |
|  | Y7 | 5000 ± 2400 | 0.42 ± 0.04 |
|  | Group | 6200 ± 3200 | 0.46 ± 0.04 |
|  | P-Value | 0.004 | 0.002 |

Data for the individual cell lines represent nine measurements; mRNA levels were determined in triplicate on three separate occasions. Data are presented as average ± S.D. Statistical comparisons were made with Student's t-test.

To verify the specificity of the MMP-1 shRNA sequences for MMP-1 mRNA, the mRNA levels of the gelatinases (MMP-2 and MMP-9), the interstitial collagenase MMP-13, and membrane bound MT-1 MMP (MMP-14) were measured in each group of cells using qRT-PCR. The MMP expression data fro each cell line was then averaged to obtain mean MMP expression levels for each group of cells. These MMPs were chosen because they are widely studied in cancer research and because MMP-13 and MT-1 MMP have similar substrate specificity as MMP-1 (Visse and Nagase (2003) *Circ. Res.* 92:827-39; Stamenkovic (2000) *Semin. Cancer Biol.* 10:415-33). No significant difference in the MMP-2, MMP-9, MMP-13, and MT-1 MMP mRNA levels were observed between cells harboring the empty vector or those with the MMP-1 shRNA (Table 2). One of the cell lines harboring the empty vector, had elevated MMP-9 expression levels, thus affecting the average of the group of cell lines. However, this clone was not removed from the pool of empty vector cell lines because the relative levels of MMP-9 expression were low when compared to MMP-1 expression for these cell (Table 1 and Table 2). In addition, including the third cell line provided a further control for variations in the expression levels of unmeasured genes.

TABLE 2

| PSUPER ™ retro insert | MMP-2 | MMP-9 | MMP-13 | MT1-MMP |
|---|---|---|---|---|
| Empty Vector | 11.2 ± 7.3 | 1000.4 ± 645.4 | 1.5 ± 1.4 | 145000 ± 46638 |
| MMP-1 shRNA | 8.8 ± 7.8 | 197.3 ± 106 | 0.5 ± 0.2 | 107000 ± 46000 |
| P-Value | 0.3 | 0.1 | 0.3 | 0.4 |

MMP mRNA levels were measured in RNA harvested from stable cell lines after a 24 hour incubation in serum-free medium and were normalized to GAPDH mRNA levels. Messenger RNA levels were determined in triplicate on three separate occasions. Data are presented as average ± S.D. Statistical comparisons were made with Student's t-test.

To confirm that the MMP-1 shRNA did not affect cell growth, the increase in metabolic activity of the cell lines from 24 to 48 hours was used as an estimation of their proliferation rate. The fold increase in metabolic activity of MDA-231 cells with the empty vector (1.63±0.359 in 24 hours) did not differ significantly from the increase in activity of the cells producing MMP-1 shRNA molecules (2.03±0.06 in 24 hours, p=0.13). Therefore, the only measured differences between the two groups of cell lines were the levels of MMP-1 mRNA and protein.

To determine whether the MMP-1 shRNA was producing a shRNA-associated interferon response in the stable cell lines, the expression levels of 11 interferon-responsive genes was compared between pools of stable cell lines (Bridge, et al. (2003) *Nat. Genet.* 34:263-4). Semi-quantitative RT-PCR revealed two genes (MxA and GBP1) with a slight (~50%) increase in expression in the MMP-1 shRNA cell lines when compared to the empty vector cell lines, and three genes (SCYB10/IP-10, MxB, and OAS1) with a modest (~35% to 50%) decrease in expression. Overall, there was no consistent upregulation of interferon-responsive gene expression to indicate that MMP-1 shRNA induced an interferon response in the MDA-231 cell lines.

EXAMPLE 4

MMP-1 siRNA-Mediated Suppression of Collagen Matrix Degradation

An in vitro collagen destruction assay was developed to determine whether the MMP-1 levels in MDA-231 cells with the empty vector were functionally capable of degrading a collagen matrix, and whether the shRNA-mediated reduction in MMP-1 was sufficient to change the invasive behavior of the cells. MDA-231 cells harboring either the empty vector or the MMP-1 shRNA were embedded in a solution of type I collagen (1 mL). The collagen was allowed to solidify at 37° C., and 1 mL of serum-free medium was layered on top of each gel. After 36 hours at 37° C., the medium was removed from each well and photographs were taken. No collagen was visible in wells containing MDA-231 cells with the empty vector. However, the collagen in wells containing cells producing the MMP-1 shRNA appeared to be intact. The medium removed from each well was weighed to quantitate the amount of medium liberated as the gel was destroyed. After 36 hours, approximately 1 mL (0.8±0.06 grams) of medium was liberated from the collagen gels containing the MDA-231 cells with the empty vector. This volume was comparable to the volume of the gel at the beginning of the experiments (1 mL), indicating that these cells had completely degraded the collagen matrix. Conversely, no medium (−0.01±0.03 grams) was liberated from collagen gels containing MDA-231 cells producing the MMP-1 shRNA. The slight decrease in the volume of medium recovered may be due to evaporation of the medium during the incubation period. These results demonstrate that MMP-1 produced by cells containing the empty vector can destroy a collagen gel, and that shRNA-mediated reduction of MMP-1 expression blocked the collagenolytic activity of the cells.

To confirm that MMP expression was responsible for destruction of the collagen gel, the pan-MMP chemical inhibitor ILOMASTAT® (25 µM/gel) or vehicle control (1% DMSO) was embedded in the collagen together with cells containing the empty vector. After 36 hours, no medium (−0.1±0.08 grams) had been liberated from the ILOMASTAT®-treated collagen gels, while cells incubated with the DMSO vehicle had liberated approximately 1 mL of medium (0.8±0.05 grams).

The three MMPs primarily responsible for degrading type 1 collagen are MMP-1, MMP-13, and the membrane bound MT1-MMP (Stamenkovic (2003) *J. Pathol.* 200:448-64). MMP-1 and MMP-13 are secreted as proenzymes and require step-wise cleavage of the propeptide (often by serine proteases) before the enzymes become active (Visse and Nagase (2003) supra). MT1-MMP requires no extracellular activation because it is embedded in the cell membrane as an active enzyme. Therefore, to distinguish between MT1-MMP-mediated destruction of the collagen gel and MMP-1 and MMP-13 destruction of the collagen gel, the serine protease inhibitor aprotinin (50 U/mL collagen) was embedded in collagen gels with MDA-231 cells containing the empty vector. After 36 hours no medium had been liberated from the collagen gels containing cells and aprotinin (0.01±0.1 grams), indicating that MMP-1 or even MMP-13 (despite its low level of expression, Table 2) was responsible for the collagenolytic activity of the MDA-231 cells containing the empty vector. Western blot analysis of the culture medium of stably transfected cells confirmed that aprotinin blocked activation of MMP-1. No detectable MMP-1 protein was observed in the medium of MDA-231 cells producing the MMP-1 shRNA, confirming the ELISA and qRT-PCR findings. However, a band representing cleaved and activated MMP-1 was clearly visible when cells containing the empty vector were grown on plastic. When these cells were embedded in the collagen gel, there were two MMP-1 protein bands representing both the 54 kD zymogen and the smaller activated form of the enzyme. Further, medium from aprotinin-treated cells contained only the higher molecular weight zymogen band. The presence of more MMP-1 protein in the medium of control cells grown on collagen further indicates that embedding MDA-231 cells in a collagen matrix stimulates a two to three-fold increase in MMP-1 expression. Cleavage of the propeptide domain of the 54 kD MMP-1 zymogen produces a 44 kD active form of the enzyme; however, smaller 24 kD MMP-1 proteins have been reported and were demonstrated to represent active MMP-1 (Clark and Cawston (1989) *Biochem. J.* 263:201-6). The results of the western blot analysis confirm that MDA-231 cells produce proteinases that can activate proMMP-1 (Benbow, et al. (1999) *Clin. Exp. Metastasis* 17:231-8) and that aprotinin is capable of blocking this activation. These results also indicate that MMP-1 is responsible for destruction of the collagen gels.

To further demonstrate that the collagenolytic activity observed was due to MMP-1, MMP-1 neutralizing antibody was embedded (1 µg antibody/mL collagen) in the collagen gel along with MDA-231 cells containing the empty vector. A monoclonal antibody against the FLAG® epitope was used as the negative control (1 µg antibody/mL collagen). At 24 hours, there was a noticeable difference in the thickness of the collagen gels. After 40 hours, the weight of medium liberated from gels containing FLAG® antibody and cells was comparable to the medium liberated from wells containing cells alone (0.78±0.03 grams), while very little medium was liberated from collagen gels containing the MMP-1 antibody and cells (0.14±0.04 grams). The small volume of medium liberated from collagen gels by MDA-231 cells incubated with the MMP-1 neutralizing antibody could be attributed to the limited effectiveness of the MMP-1 neutralizing antibody in blocking MMP-1 activity for a long period of time; by 50 hours the collagen gel was completely destroyed, indicating that MMP-1 production by these cells could eventually overwhelm the neutralizing antibody. Conversely, when the MDA-231 cell lines producing MMP-1 shRNA were incubated in collagen gels for as long as five days, there was no collagen gel destruction. These results indicate that the MDA-231 cell-mediated destruction of collagen is a result of MMP-1 expression, and that blocking MMP-1 expression with an MMP-1 shRNA blocks the ability of MDA-231 cells to degrade a type 1 collagen matrix.

EXAMPLE 5

MMP-1 siRNA-Mediated Inhibition of Tumor Cell Formation and Growth

The in vivo efficacy of the shRNA-mediated reduction of MMP-1 in the MDA-231 cells was analzyed. Nude mice were injected in the fourth inguinal mammary fat pad with MDA-231 cells containing either the empty vector or the MMP-1 shRNA. At week 6, tumors began to appear in the inguinal pad of several mice and at week 11, the mice were sacrificed. The frequency of tumor formation in mice injected with the empty vector cell lines (57%, n=23) were not significantly greater than mice injected with MMP-1 shRNA producing cells (36%, n=23; p=0.11, Fisher's exact test). However, at the time of sacrifice, the average tumor size in mice injected with cells containing the empty vector ($1217 \pm 334$ mm$^3$; mean±s.e.; n=13) was significantly greater (p=0.027, Student's t-test) than the average tumor size in mice injected with cells producing the MMP-1 shRNA ($272 \pm 117$ mm$^3$; mean±s.e.; n=10). Furthermore, exponential curve fits of the average weekly tumor sizes generated by the EXCEL™ program revealed that the tumor cells producing MMP-1 were growing at a faster rate (tumor volume=$2.4874e^{0.5431 week}$, $R^2$=0.9412) than tumor cells not producing MMP-1 (tumor volume $21.802e^{0.1892 week}$, $R^2$ 0.2883). Examination of the mice at autopsy revealed no macroscopic metastases to any organs in the peritoneal cavity, the lungs, or the brain. Furthermore, histological slides of these organs revealed no microscopic metastases. These data indicate that MMP-1 is not necessary for tumor formation, but that it contributes to the growth of primary tumors in this mouse model.

While mice lack a homolog of MMP-1, transgenic expression of MMP-1 in mice has been used to investigate its role in tumorigenesis. Over-expression of human MMP-1 in mouse skin results in an increased susceptibility to tumorigenesis (D'Armiento, et al. (1995) *Mol. Cell. Biol.* 15:5732-9) and, not wishing to be bound by theory, it is believed that MDA-231 cells require the collagenolytic activity of MMP-1 to break down the fibrous stroma within the mammary fat pad to remove a physical barrier to growth. Video microscopy have demonstrated that inhibiting collagen degradation does not block tumor cell migration through a matrix, but rather alters the type of movement into an amoeboid motion that leaves the collagen gel intact (Stamenkovic (2003) supra; Hegerfeldt, et al. (2002) *Cancer Res.* 62:2125-30; Wolf, et al. (1993) *J. Cell. Biol.* 160:267-277). However, degradation of ECM molecules does more than facilitate cell mobility by removing a physical barrier. The ECM contains growth factors that are liberated by breakdown of matrix proteins. MMP-1, in particular, is capable of cleaving the proteoglycan perlecan, which can release basic fibroblast growth factor (Whitelock, et al. (1996) *J. Biol. Chem.* 271:10079-86). MMP-1 can also cleave insulin-like growth factor (IGF) binding proteins that are present in the ECM, thereby increasing the availability of IGF and increasing cell proliferation (Fowlkes, et al. (1997) *J. Biol. Chem.* 269:25742-6).

What is claimed is:

1. A method for inhibiting the synthesis or expression of matrix metalloproteinase 1 comprising contacting a cell expressing matrix metalloproteinase 1 with an siRNA that has a sequence complementary to at least part of a matrix metalloproteinase 1 nucleic acid sequence thereby specifically inhibiting the synthesis or expression of matrix metalloproteinase 1, wherein the siRNA is set forth in SEQ ID NO:1 and SEQ ID NO:2.

2. A method for suppressing invasion or metastasis of a tumor cell comprising contacting a tumor cell expressing a matrix metalloproteinase 1 with a sufficient amount of an siRNA that specifically inhibits the synthesis or expression of the matrix metalloproteinase 1 thereby suppressing the invasion or metastasis of the tumor cell, wherein the siRNA is set forth in SEQ ID NO:1 and SEQ ID NO:2.

3. A method of treating or managing cancer comprising administering to a patient in need of such treatment or management a therapeutically effective amount of an siRNA that inhibits the synthesis or expression of matrix metalloproteinase 1 thereby treating or managing the cancer, wherein the siRNA is set forth in SEQ ID NO:1 and SEQ ID NO:2.

* * * * *